US012364559B2

(12) United States Patent
Shepard et al.

(10) Patent No.: US 12,364,559 B2
(45) Date of Patent: Jul. 22, 2025

(54) ACTUATION LINE STORAGE SYSTEMS AND METHODS

(71) Applicant: W. L. Gore & Associates, Inc., Newark, DE (US)

(72) Inventors: Michael J. Shepard, Flagstaff, DE (US); James D. Silverman, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 1004 days.

(21) Appl. No.: 17/433,156

(22) PCT Filed: Feb. 22, 2019

(86) PCT No.: PCT/US2019/019131
§ 371 (c)(1),
(2) Date: Aug. 23, 2021

(87) PCT Pub. No.: WO2020/171819
PCT Pub. Date: Aug. 27, 2020

(65) Prior Publication Data
US 2022/0133423 A1 May 5, 2022

(51) Int. Cl.
*A61B 17/00* (2006.01)
*A61B 34/00* (2016.01)
(52) U.S. Cl.
CPC ........ *A61B 34/71* (2016.02); *A61B 17/00234* (2013.01); *A61B 2017/00336* (2013.01);
(Continued)

(58) Field of Classification Search
CPC .............. A61B 34/71; A61B 17/00234; A61B 2017/00336; A61B 2017/00367;
(Continued)

(56) References Cited

U.S. PATENT DOCUMENTS

| 3,443,771 A | 5/1969 | Doty |
| 4,935,027 A | 6/1990 | Yoon |

(Continued)

FOREIGN PATENT DOCUMENTS

| CN | 101945621 A | 1/2011 |
| CN | 102281839 A | 12/2011 |

(Continued)

OTHER PUBLICATIONS

International Preliminary Report on Patentability received for PCT Patent Application No. PCT/US2019/019131, mailed on Sep. 2, 2021, 9 pages.

(Continued)

*Primary Examiner* — Gary Jackson
*Assistant Examiner* — Sebastian X Lukjan

(57) ABSTRACT

A medical device deployment apparatus that employs a first actuation line and a second actuation line, whereby a delay is sought between initiation of the actuation of the first actuation line and actuation of the second actuation line. Prior to actuation, the first actuation line includes sequentially aligned multiple loops, wherein the multiple loops provide predefined slack to delay linear actuation of the first actuation line when tension is applied to both the first and second actuation lines.

23 Claims, 9 Drawing Sheets

(52) U.S. Cl.
CPC .............. *A61B 2017/00367* (2013.01); *A61B 2017/0046* (2013.01); *A61B 2034/715* (2016.02)

(58) Field of Classification Search
CPC ....... A61B 2017/0046; A61B 2034/715; A61F 2/9517; A61F 2/962; A61F 2/95
See application file for complete search history.

(56) References Cited

U.S. PATENT DOCUMENTS

| | | |
|---|---|---|
| 6,224,627 B1 | 5/2001 | Armstrong et al. |
| 6,349,894 B1 | 2/2002 | Daoud et al. |
| 6,352,561 B1 | 3/2002 | Leopold et al. |
| 6,551,350 B1 | 4/2003 | Thornton et al. |
| 8,459,446 B2 | 6/2013 | Kozlowski |
| 9,375,308 B2 | 6/2016 | Norris |
| 9,849,016 B2 | 12/2017 | Beard et al. |
| 10,004,620 B2 | 6/2018 | Treacy et al. |
| 2003/0167071 A1 | 9/2003 | Martin et al. |
| 2004/0138734 A1 | 7/2004 | Chobotov et al. |
| 2005/0080483 A1 | 4/2005 | Solem et al. |
| 2006/0000618 A1 | 1/2006 | Cho et al. |
| 2007/0112355 A1 | 5/2007 | Salahieh et al. |
| 2008/0112680 A1 | 5/2008 | McGranahan |
| 2010/0211052 A1 | 8/2010 | Brown et al. |
| 2012/0093473 A1 | 4/2012 | Cox et al. |
| 2013/0268048 A1 | 10/2013 | Watson et al. |
| 2013/0287356 A1 | 10/2013 | Solheid et al. |
| 2014/0066948 A1 | 3/2014 | Soutorine et al. |
| 2014/0107760 A1* | 4/2014 | Holm .................. A61F 2/97 623/1.12 |
| 2014/0277366 A1 | 9/2014 | Cummins et al. |
| 2015/0182227 A1 | 7/2015 | Le et al. |
| 2015/0282881 A1* | 10/2015 | Beard ............... A61B 17/3468 606/130 |
| 2016/0252110 A1 | 9/2016 | Galloway et al. |
| 2016/0296352 A1 | 10/2016 | Ryan et al. |
| 2017/0035590 A1 | 2/2017 | Watson et al. |
| 2017/0273812 A1 | 9/2017 | Macatangay et al. |
| 2017/0371107 A1 | 12/2017 | Rudenick et al. |
| 2018/0116743 A1 | 5/2018 | Burbank et al. |
| 2019/0191967 A1 | 6/2019 | Yamamoto et al. |
| 2020/0206391 A1 | 7/2020 | Eaton et al. |
| 2023/0024717 A1 | 1/2023 | Beard et al. |

FOREIGN PATENT DOCUMENTS

| | | |
|---|---|---|
| CN | 102656676 A | 9/2012 |
| CN | 103370019 A | 10/2013 |
| CN | 106455916 A | 2/2017 |
| CN | 107822692 A | 3/2018 |
| CN | 207561912 U | 7/2018 |
| GB | 1590967 A | 6/1981 |
| JP | 03-041883 U | 4/1991 |
| JP | 2001-506902 A | 5/2001 |
| WO | 98/27894 A1 | 7/1998 |
| WO | 2010/104566 A1 | 9/2010 |
| WO | 2012/032645 A1 | 3/2012 |
| WO | 2015/134917 A2 | 9/2015 |
| WO | 2017/198708 A1 | 11/2017 |

OTHER PUBLICATIONS

International Preliminary Report on Patentability received for PCT Patent Application No. PCT/US2019/067107, mailed on Jun. 30, 2022, 9 pages.
International Search Report and Written Opinion received for PCT Patent Application No. PCT/US2019/019131, mailed on Oct. 24, 2019, 17 pages.
International Search Report and Written Opinion received for PCT Patent Application No. PCT/US2019/067107, mailed on Aug. 19, 2020, 14 pages.

* cited by examiner

ACTUATION LINE STORAGE SYSTEMS AND METHODS

CROSS-REFERENCE TO RELATED APPLICATION

This application is a national phase application of PCT Application No. PCT/US2019/019131, internationally filed on Feb. 22, 2019, which is herein incorporated by reference in its entirety for all purposes.

FIELD

The present disclosure relates generally to actuation line storage systems and, more specifically, to actuation line storage systems for delayed actuation during medical device deployment and associated apparatuses and methods thereof.

BACKGROUND

Various medical device delivery systems have multiple actuators including multiple wires, strings, fibers, or other suitable actuation lines that control actuation of one or more components (sleeve delivery constraint and/or an expandable implantable device, for example). Among other issues, systems having multiple actuators may be relatively more complex, require larger handles and/or thicker catheters to accommodate additional actuation lines, and may have increased risk of malfunction from tangling, knotting, or interference of actuation lines.

SUMMARY

According to a first example ("Example 1"), a medical device deployment apparatus employs a first actuation line and a second actuation line, whereby a delay is sought between initiation of actuation of the first actuation line and initiation of actuation of the second actuation line. The medical device comprises, prior to actuation, the first actuation line including sequentially aligned multiple loops. The multiple loops provide predefined slack to delay linear actuation of the first actuation line when tension is applied to both the first and second actuation lines.

According to a second example ("Example 2"), the medical device deployment apparatus further to Example 1 further comprises a release material, wherein the multiple loops are releasably adhered to the release material to maintain the sequence of the multiple loops prior to actuation.

According to a third example ("Example 3"), further to Example 2 the release material comprises a tube.

According to a fourth example ("Example 4"), further to Example 3, the multiple loops are releasably adhered inside of the tube.

According to a fifth example ("Example 5"), further to any one of Examples 2 to 4, the second actuation line is routed through the tube.

According to a sixth example ("Example 6"), further to any preceding Example, the multiple loops define a repeating figure-8 pattern.

According to a seventh example ("Example 7"), a medical device deployment apparatus employs a first actuation line and a second actuation line, whereby a delay is sought between initiation of actuation of the first actuation line and initiation of actuation of the second actuation line, the medical device deployment apparatus comprising prior to actuation, the first actuation line being releasably adhered to a release material in the form of sequential multiple windings; wherein the multiple windings provide predefined slack to delay linear actuation of the first actuation line when tension is applied to both the first and second actuation lines.

According to an eighth example ("Example 8"), further to Example 7, the release material comprises a tube.

According to a ninth example ("Example 9"), further to Example 7, wherein the release material comprises a sheet.

According to a tenth example ("Example 10"), further to any one of Examples 7 to 9, wherein the multiple windings comprise multiple loops.

According to an eleventh example ("Example 11"), further to Example 10, the multiple windings comprise a figure-8 configuration.

According to a twelfth example ("Example 12"), further to any one of Examples 7 to 11, the multiple windings comprise an accordion folding of the second actuation line.

According to a thirteenth example ("Example 13"), a fiber storage system for an actuation assembly comprises a first actuation line defining a first portion, a second portion, and an intermediate portion extending between the first portion and the second portion, the intermediate portion configured in a slack pattern; and a release material having an inner surface defining an inner lumen of the release material, the intermediate portion of the first actuation line being releasably maintained in the slack pattern by an inner aspect of the release material such that, upon tensioning the first portion of the first actuation line, the intermediate portion is serially released from the inner aspect of the release material according to the slack pattern without transferring tension to the second portion of the first actuation line.

According to a fourteenth example ("Example 14"), further to Example 13, the slack pattern includes a helical portion.

According to a fifteenth example ("Example 15"), further to any one of Examples 13 or 14, wherein the slack pattern includes multiple sequentially aligned loops.

According to a sixteenth example ("Example 16"), further to any one of Examples 13 to 15, the slack pattern includes multiple, sequentially aligned figure-8's.

According to a seventeenth example ("Example 17"), further to any one of Examples 13 to 16, the slack pattern includes a diametric taper.

According to an eighteenth example ("Example 18"), further to any one of Examples 13 to 17, the system further comprises a second actuation line defining a first portion, a second portion, and an intermediate portion, the second actuation line extending through the slack pattern of the first actuation line.

According to a nineteenth example ("Example 19"), further to Example 18, the first portion of the first actuation line is operably coupled to the first portion of the second line such that tension on the first actuation line is applied concurrently to the second actuation line, and further wherein the slack pattern of the first actuation line decouples the second portions of the first and second lines such that the first portion of the first line is tensionable without tensioning the second portion of the second actuation line.

According to a twentieth example ("Example 20"), further to any one of Examples 13 to 19, the release material includes a hollow tube having an inner lumen defining the inner aspect of the release material.

According to another example ("Example 21"), further to any one of Examples 17 to 20, the system further comprises an expandable medical device; and a sleeve diametrically constraining the medical device; wherein the first actuation line is configured to release the sleeve and the second actuation line is configured to retract the sleeve.

According to another example ("Example 22"), a method of deploying the expandable medical device of the medical system of Example 21 comprises: tensioning the first actuation line to pull back the sleeve from the expandable medical device; and tensioning the second actuation line to release the sleeve from the expandable medical device; wherein tension applied to the first portion of the second actuation line translates to tension to the second portion of the second actuation line, and wherein tension applied to the first portion of the first actuation line is translated to the intermediate portion of the second actuation line and not to the second portion of the second actuation line.

The foregoing examples are provided for illustrative purposes and should not be considered to limit the inventive scope of the various concepts addressed in the remainder of this disclosure.

BRIEF DESCRIPTION OF THE DRAWINGS

The accompanying drawings are included to provide a further understanding of the disclosure and are incorporated in and constitute a part of this specification, illustrate embodiments, and together with the description serve to explain the principles of the disclosure.

DETAILED DESCRIPTION

Various aspects of the present disclosure relate to actuation line storage systems for medical device deployment apparatuses (e.g., to facilitate delayed actuation operations during a medical device deployment sequence). Such systems generally include a delivery catheter, an implantable, expandable medical device, and a sleeve, sheath, or other constraint diametrically constraining the medical device in a compressed, delivery configuration. In certain scenarios, medical device deployment systems can also include wires, strings, fibers, or other suitable actuation lines capable of selectively actuating various aspects of the deployment apparatus such as, for example, the sleeve, the medical device, and/or other components as desired.

Various examples of actuation line storage systems according to the instant disclosure, require less space, remove or reduce the potential for actuation line tangling, knotting, or other malfunctions during operation, and achieve other additional or alternative features and advantages over known actuation line systems.

Figure 1:
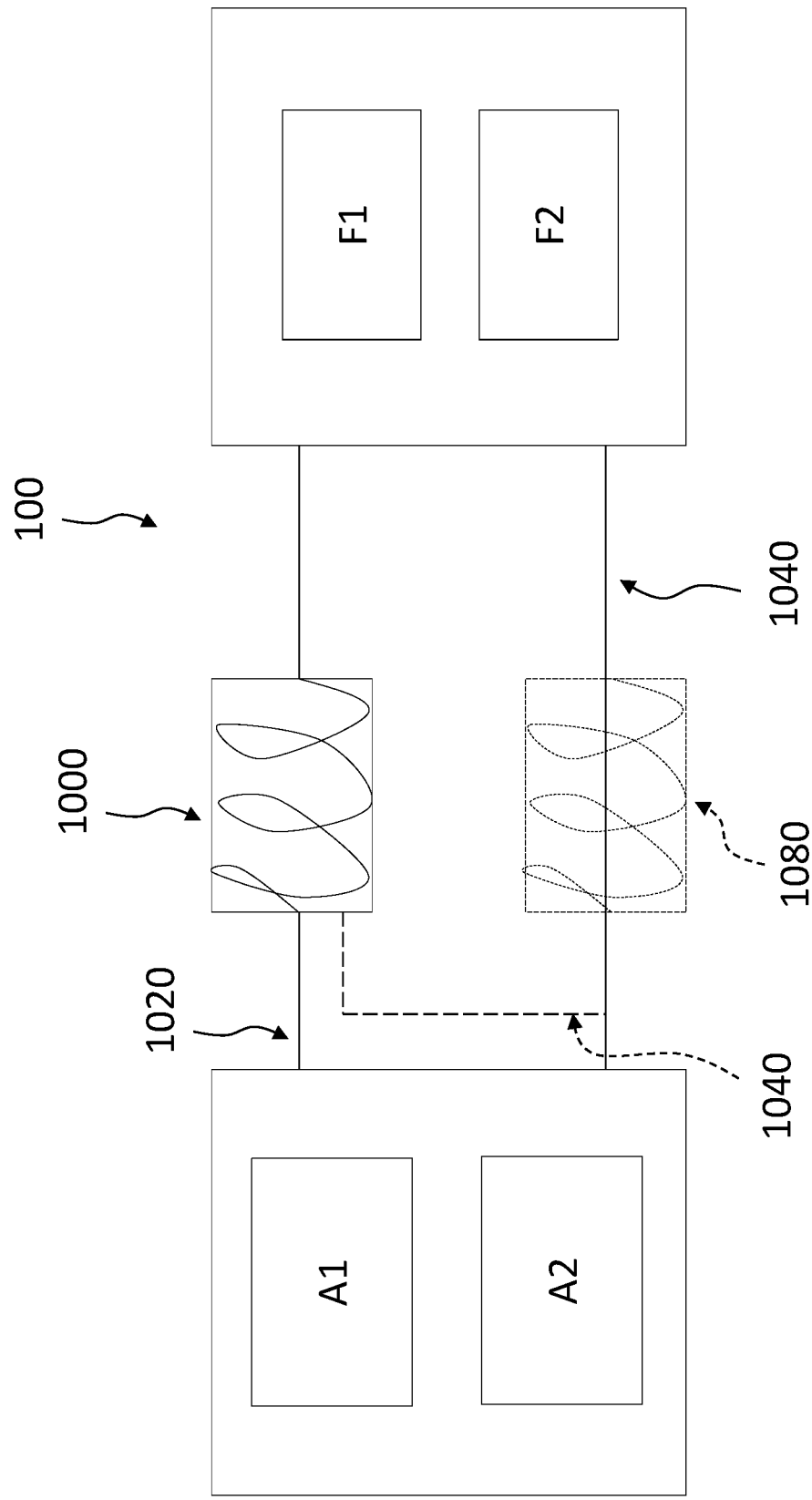
FIG. 1 is a schematic view of a medical device deployment system, according to some embodiments.

FIG. 1 is a schematic representation of a medical device deployment system 100 including an actuation line storage system 1000, according to some examples. As shown, the medical device deployment system 100 also includes a first actuating mechanism A1, a second actuating mechanism A2, a first actuation line 1020, a second actuation line 1040, a first actuation element E1, and a second actuation element E2. The first actuation line 1020 is actuatable via the first actuating mechanism A1 to initiate the first actuation element E1 and the second actuation line 1040 is actuatable via the second actuating mechanism A2 to initiate the second actuation element E2.

Figure 2:
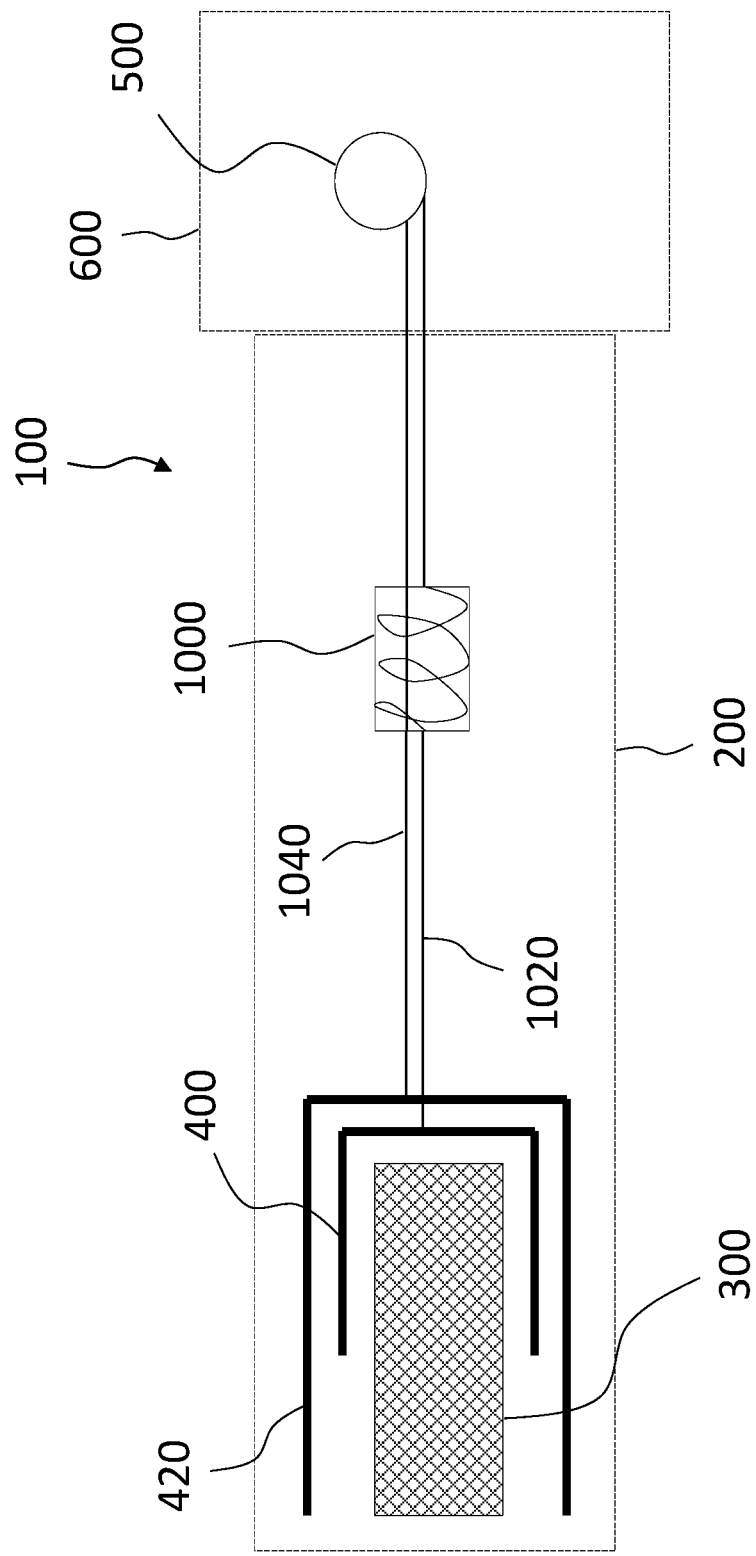
FIG. 2 is a perspective view of a medical device deployment system, according to some embodiments.

The first and second actuating mechanisms A1 and A2 may be part of an actuation handle, such as actuation handle 600 shown in FIG. 2. For example, the actuating mechanisms can be buttons, toggles, switches, dials, rotatable cuffs, or other actuators capable of causing actuation of the first and second actuation lines 1020 and 1040, respectively. The first and second actuating mechanisms A1 and A2 need not be separate components. For example, the first and second actuating mechanisms may be part of a single button, toggle, switch, dial, rotatable cuff, or other actuating mechanism to which both the first and second actuation lines 1020 and 1040 are coupled, but which is capable of acting as a first actuation mechanism A1 for the first actuation line 1020 and as a second actuation mechanism A2 for the second actuation line 1040.

In general terms, the first actuation mechanism A1 operates to manipulate (e.g., tension) the first actuation line 1020, which operates to then actuate the first actuation element E1 of the system 100. For example, the first actuation element E1 of the system 100 could be the retraction of an outer sleeve overlaying a medical device and a constraining sleeve maintaining a portion of the medical device at a constrained diameter or the expansion and/or deployment of the medical device.

In turn, the second actuation mechanism A2 operates to manipulate (e.g., tension) the second actuation line 1040 to then cause actuation of the second actuation element E2 of the system 100. As an example, the second actuation element E2 may be the longitudinal displacement of a constraining sleeve over an expandable medical device, such as the constraining sleeve 400 and the medical device 300 shown in FIG. 2.

As shown, the first actuation line 1020 passes through the actuation line storage system 1000, which holds a desired length or portion of the first actuation line 1020. This length, or stored portion of the first actuation line 1020, can serve as a timing or delay mechanism such that a desired amount of slack, or stored material of the actuation line 1020 is tensioned before the actuation line 1020 operates to cause the first actuation element E1 to perform.

As indicated in FIG. 1, the second actuation line 1080 optionally passes through the actuation line storage system 1000, as shown by the dashed line 1040 in FIG. 1. In some instances, the second actuation line 1040 may pass through the actuation line storage system 1000 without interacting with the first actuation line 1020 to prevent tangling or interference between the actuation lines. For example, the second actuation line 1040 may pass straight through the actuation line storage system 1000 while the first actuation line 1020 may be configured in a predefined slack pattern, such as sequentially wound around the actuation line storage system 1000, for example. In other instances, the second actuation line 1040 may not pass through the actuation line storage system 1000 but may be routed outside of the storage system 1000 or in another configuration entirely.

In some embodiments, the system 100 may also include a second actuation line storage system 1080. Thus, the first actuation line 1020 can pass through the actuation line storage system 1000, which holds a desired length or portion of the first actuation line 1020, and the second actuation line 1040 can pass through the second actuation line storage system 1080, which holds a desired length or portion of the second actuation line 1080. In this way, both actuation lines may be arranged to provide various amounts of delay to the actuation elements as desired. In other terms, the actuation line storage system 1000 can include a first actuation line storage 1000, a second actuation line storage 1080, or both a first and second actuation line storage depending upon the actuation elements and/or the amount of delay desired in the system 100.

Though two actuation lines and storage systems are described above, it should be known that any number of actuation lines and storage systems may be used depending on the complexity of the delivery system. For example, in some instances, a delivery system may have more than one constraining sleeve, more than one medical device, or multiple actuation elements for various components. Thus, the system may include more than two actuation lines and/or storage systems as desired.

FIG. 2 shows a delivery system 100, according to some examples. As shown, the delivery system 100 includes a catheter body 200, a medical device 300, an optional first constraint 400 constraining a first portion 320 of the medical device 300 in a delivery configuration, an optional second constraint 420 constraining a second portion 340 of the medical device 300 in the delivery configuration, an actuation mechanism 500 located within an actuation handle 600, a first actuation line 1020 configured to manipulate various elements of the delivery system 100 such as retracting or releasing the first constraint 400, and a second actuation line 1040 configured to manipulate various elements of the delivery system 100 such as retracting or releasing the second constraint 420, inflating a balloon, expanding an implantable device, deploying a medical device, and/or other similar elements. The delivery system 100 also includes an actuation line storage system 1000 located within the delivery system 100. Though shown within the catheter body 200, the actuation line storage system 1000 can be located at any suitable location within the delivery system 100 such as, for example, in the actuation handle 600.

Figure 3:
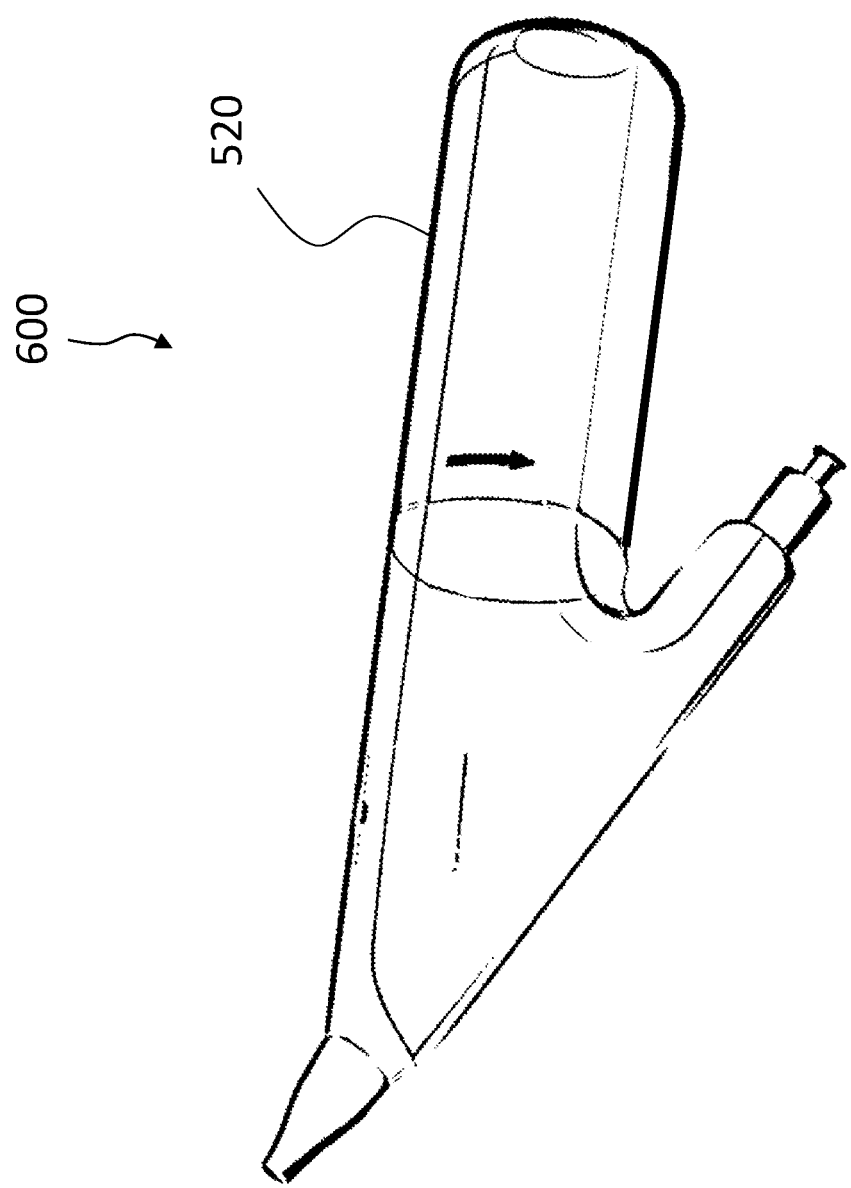
FIG. 3 is a perspective view of a medical device deployment handle, according to some embodiments.

FIG. 3 is a perspective view of an actuation handle 600, according to some embodiments. As shown, the actuation handle 600 includes an actuator 520 configured to initiate actuation of the actuation mechanism 500 (FIG. 2). The actuator 520 can be, for example, a button, toggle, switch, rotatable cuff, or any other exterior mechanism capable of being pressed, rotated, or otherwise manipulated by the operator to initiate actuation of the actuation mechanism 500 within the actuation handle 600. For example, FIG. 3 shows an actuator 520 in the form of a rotatable cuff. When rotated in the direction of the arrow, the actuator 520 initiates actuation of the actuation mechanism 500 and, in turn, initiates actuation of the first and second actuation lines 1020, 1040.

Figure 4:
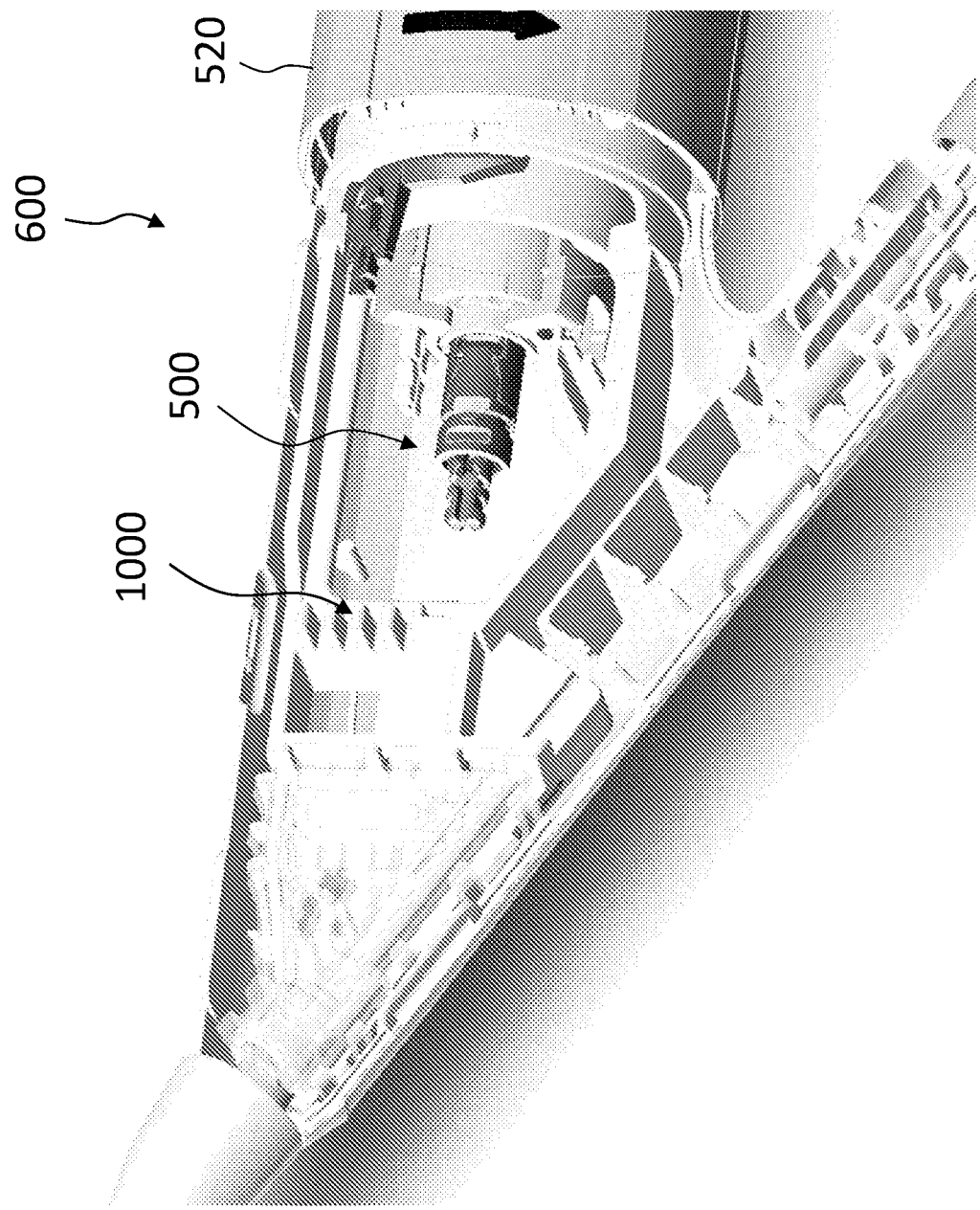
FIG. 4 is an interior view of a medical device deployment handle, according to some embodiments.

FIG. 4 is an interior view of an actuation handle 600, according to some embodiments. As shown, the actuation mechanism 500 is coupled to or otherwise interacts with the actuator 520 such that, when the operator actuates the actuator 520, the actuation mechanism 500 is also initiated. Though not shown in FIG. 4, the first and second actuation lines 1020, 1040 can be fixed to the actuation mechanism 500. Thus, when actuation of the actuation mechanism 500 is initiated, tension is simultaneously applied to the first and second actuation lines 1020, 1040 and, in turn, applied to the first actuation element E1 and second actuation element E2. The actuation line storage system 1000 can also be located within the actuation handle 600. For example, in some instances, the actuation line storage system 1000 can be fixed at the location denoted by the arrow in FIG. 4.

Figure 5:
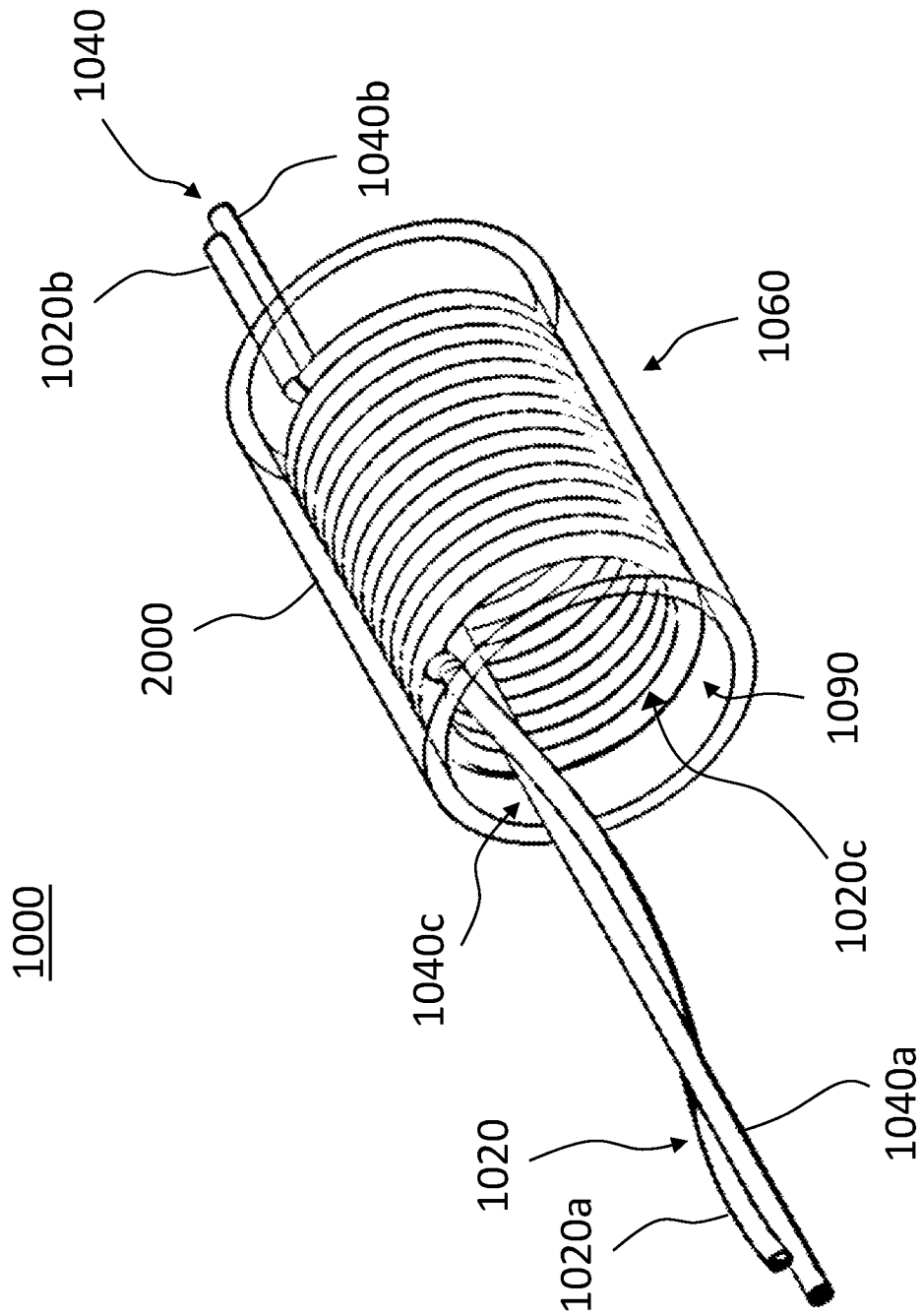
FIG. 5 is a perspective view of an actuation line storage apparatus, according to some embodiments.

FIG. 5 shows an actuation line storage system 1000, according to some embodiments. The actuation line storage system 1000 includes a first actuation line 1020, an actuation line storage portion 1060, and a second actuation line 1040. The first actuation line 1020 defines a first portion 1020a, a second portion 1020b, and an intermediate portion 1020c extending between the first portion 1020a and the second portion 1020b. In some embodiments, the first portion 1020a is coupled to the first actuation mechanism A1 such that actuation of the first actuation mechanism A1 tensions the first portion 1020a of the first actuation line 1020. The second portion 1020b is coupled to the first actuation element E1 which, in some examples, may be the constraining sleeve 400 overlaying the medical device 300, as shown in FIG. 2. In some embodiments, the intermediate portion 1020c is configured in a slack pattern. In other terms, the intermediate portion 1020c has an amount of predefined slack or desired length or portion of the first actuation line 1020 suitable to delay actuation of the first actuation element E1 element E1. For example, retraction of the constraining sleeve 400 may be delayed by the amount of slack located within the actuation line storage system 1000.

In some embodiments, the slack pattern of the first actuation line 1020 includes multiple, sequential windings which unwind or release sequentially when tension is applied to the first portion 1020a of the first actuation line 1020. These windings allow the first portion 1020a of the first actuation line 1020 to be tensioned without immediate transfer of the tension to the second portion 1020b of the first actuation line 1020, thus delaying actuation of the first actuation element E1.

As shown, the second actuation line 1040 may pass through the actuation line storage portion 1060. The second actuation line 1040 also includes a first portion 1040a, a second portion 1040b, and an intermediate portion 1040c. In some embodiments, the second actuation line 1040 extends through the actuation line storage portion 1060 in a substantially straight configuration so as not to interfere or entangle with the first actuation line 1020. Because the second actuation line 1040 is not arranged in a slack patter and does not contain a predefined amount of slack, actuation of the second actuation line 1040 can be initiated before actuation of the first actuation line 1020, thereby actuating the second actuation element E2 before the first actuation element E1. For example, the constraining sleeve 400 may be retracted before the medical device 300 is deployed and/or released into the body or vice versa.

In some embodiments, the actuation line storage portion 1060 includes a release material 2000. The release material 2000 can be any of a tube, a sheet, or any other surface upon which the intermediate portion 1020c of the first actuation line 1020 can be releasably adhered and maintained in the slack pattern prior to actuation. In some examples, the release material 2000 can include fluorinated ethylene propylene (FEP), polytetrafluoroethylene (PTFE), or other suitable materials capable of releasably maintaining the first actuation line 1020 in the slack pattern.

In some embodiments, the release material 2000 includes a hollow tube having an inner lumen defining an inner surface 1090. The intermediate portion 1020c of the first actuation line 1020 is releasably adhered to the inner surface 1090 of the tube. In other terms, the intermediate portion 1020c can be maintained in the slack pattern by the inner surface 1090 of the release material 2000 such that, upon tensioning the first portion 1020a of the first actuation line 1020, the intermediate portion 1020c is serially or sequentially released from the inner surface 1090 of the release material 2000. In some embodiments, the slack pattern includes a helical portion forming the multiple, sequentially aligned loops, which are adhered to the inside surface 1090 of the tube, as shown in FIG. 5.

Though not shown in FIG. 5, in some instances, the first portion 1020a of the first actuation line 1020 is operably coupled to the first portion 1040a of the second actuation line 1040 such that tension applied to the first actuation line 1020 is applied concurrently to the second actuation line 1040. In some embodiments, the slack pattern of the first actuation line 1020 then decouples the second portions 1020b and 1040b of the first and second actuation lines 1020 and 1040, such that the first portion 1020a of the first actuation line 1020 is tensionable without tensioning the second portion 1040b of the second actuation line 1040.

Figure 6:
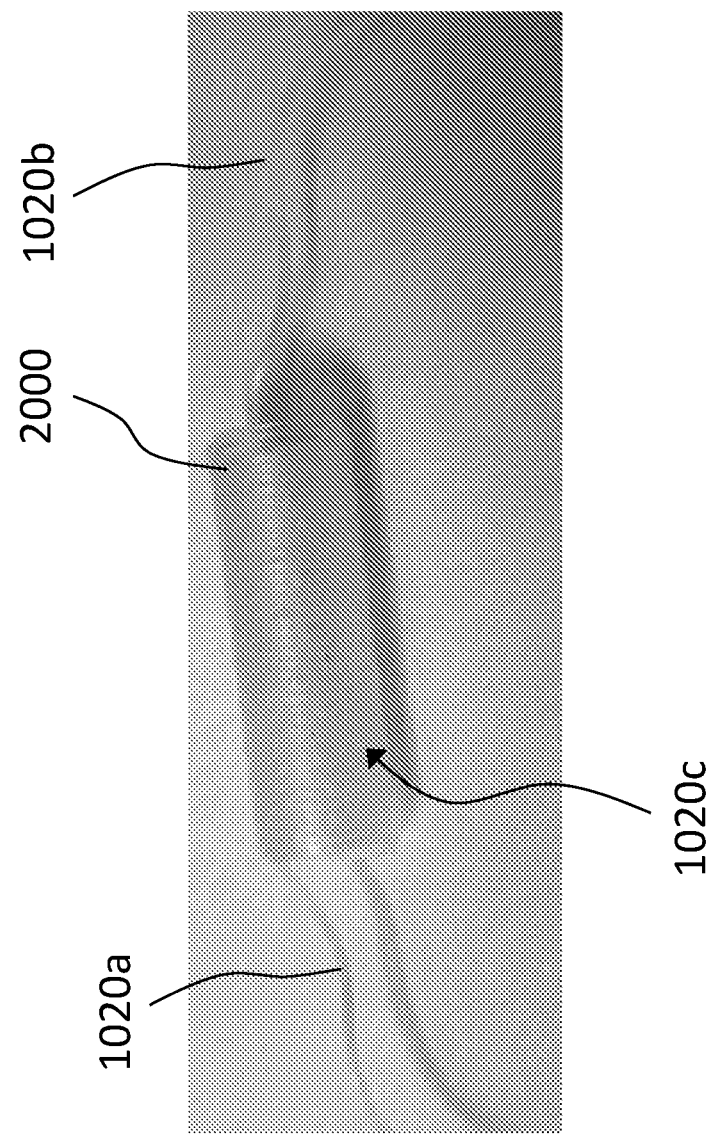
FIG. 6 is an image of actuation line storage apparatus of FIG. 1, according to some embodiments.

FIG. 6 shows an image of the actuation line storage system 1000 of FIG. 5, according to some embodiments. As discussed above, the first actuation line 1020 is wound around the inner surface 1090 of the tube, forming multiple, sequentially aligned loops. Though not shown, the second actuation line 1040 can be routed through the center of the tube so that it does not touch or interfere with the first actuation line 1020 as it releases from the inner surface 1090 of the tube. This reduces the risk of the first and second actuation lines 1020 and 1040 tangling or interfering with one another and causing malfunction of the deployment system 1000.

Figure 7:
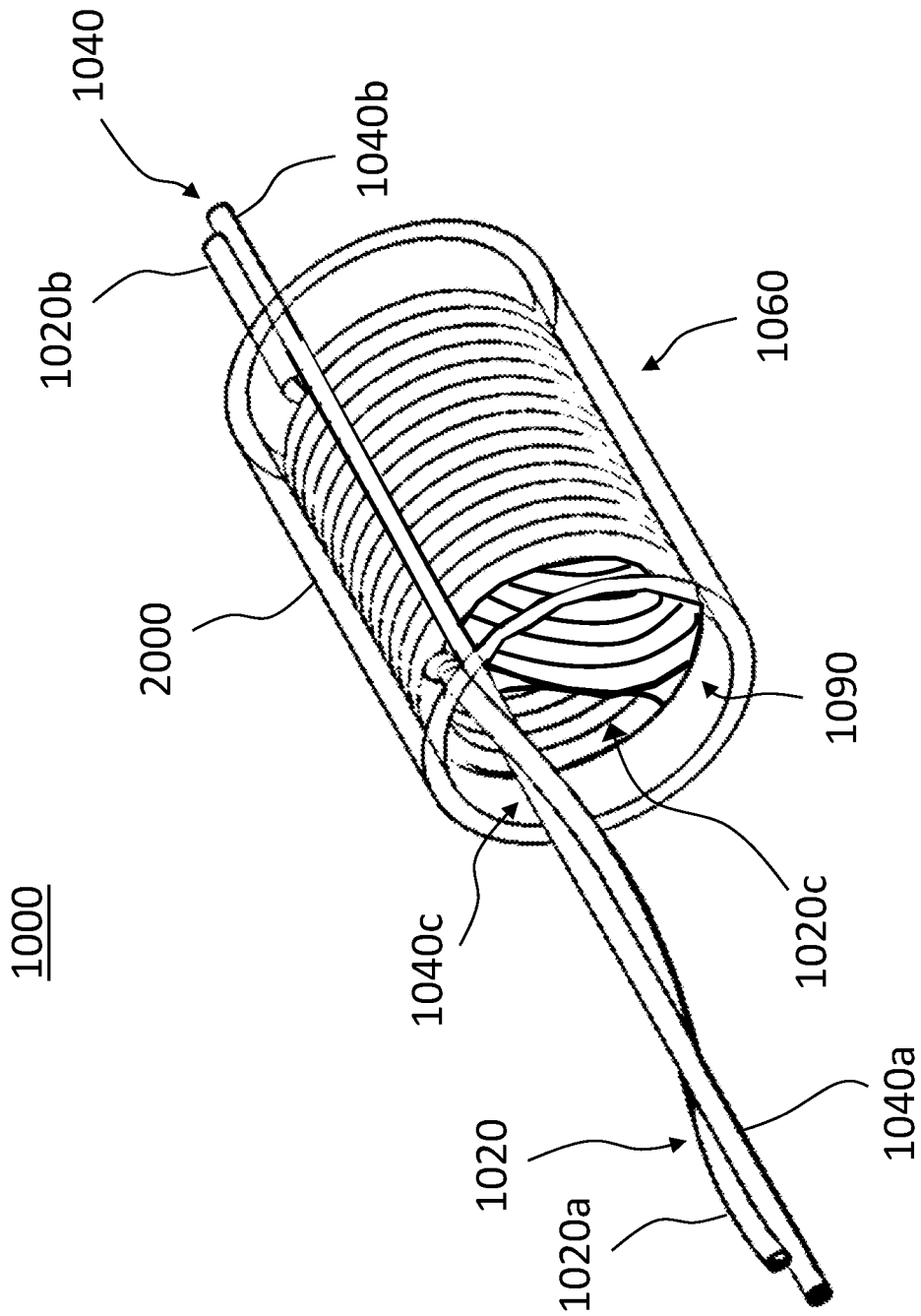
FIG. 7 is a perspective view of an actuation line storage apparatus, according to some embodiments.

FIG. 7 shows an actuation line storage system 1000, according to some embodiments. As shown, the slack pattern of the first actuation line 1020 can define a repeating, figure-eight pattern. Like the looped slack pattern described with reference to FIG. 5, the first actuation line 1020 is wound sequentially around the inner surface 1090 of the tube in a repeating, figure eight pattern. The second actuation line 1040 can then be routed through either a first aperture 1120 or a second aperture 1140 of the figure-eight pattern so as not to interfere or entangle with the first actuation line 1020 as it serially or sequentially releases from the inner surface 1090 of the tube.

Figure 8:
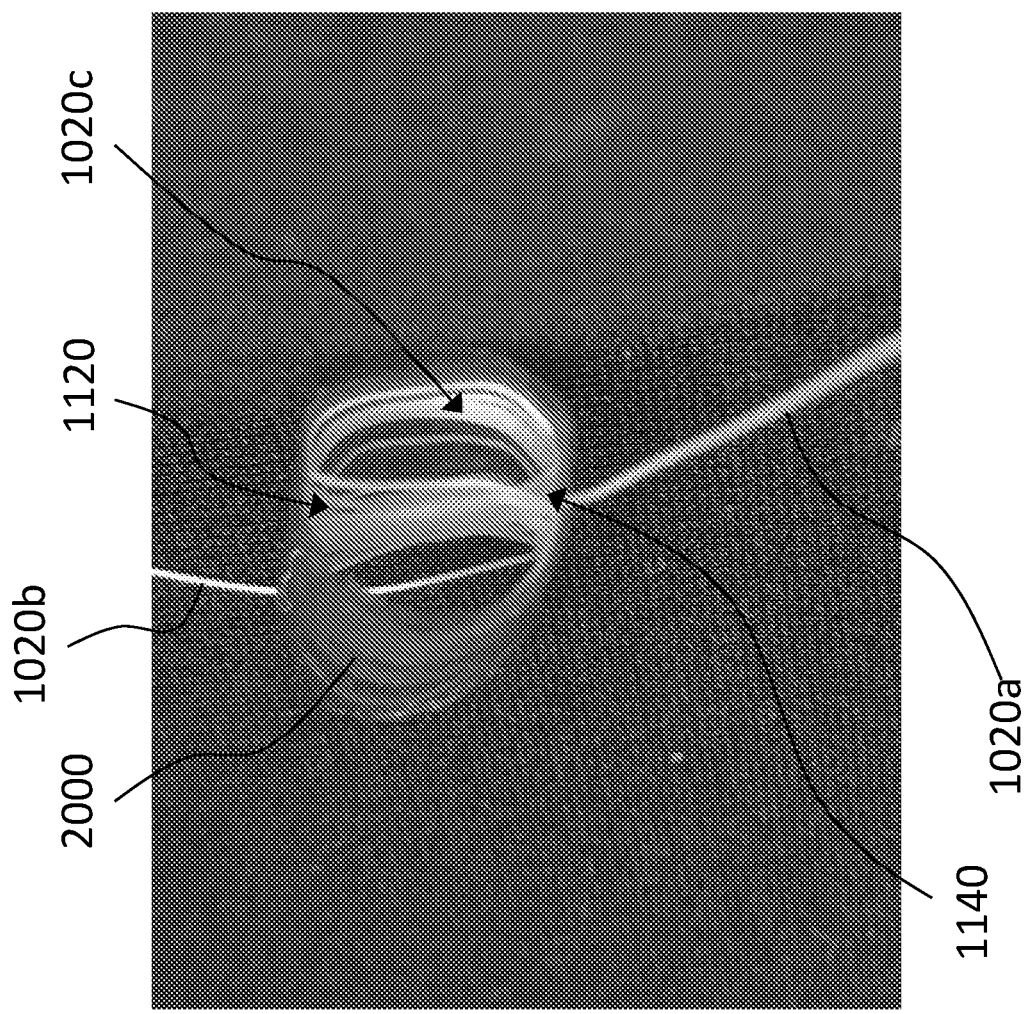
FIG. 8 is an image of the actuation line storage apparatus of FIG. 5, according to some embodiments.

FIG. 8 shows an image of the actuation line storage system 1000 of FIG. 7, according to some embodiments. As shown, the first actuation line 1020 is wound around the inner surface 1090 of the tube in a repeating, figure-eight pattern. Though not shown in FIG. 8, the second actuation line 1040 can be routed through either the first aperture 1120 or the second aperture 1140 so that the second actuation line 1040 does not interfere with the first actuation line 1020 as it releases from the inner surface 1090 of the tube. As discussed above, this reduces the risk of the first and second actuation lines 1020 and 1040 tangling or interfering with one another and causing malfunction of the deployment system 1000.

Figure 9:
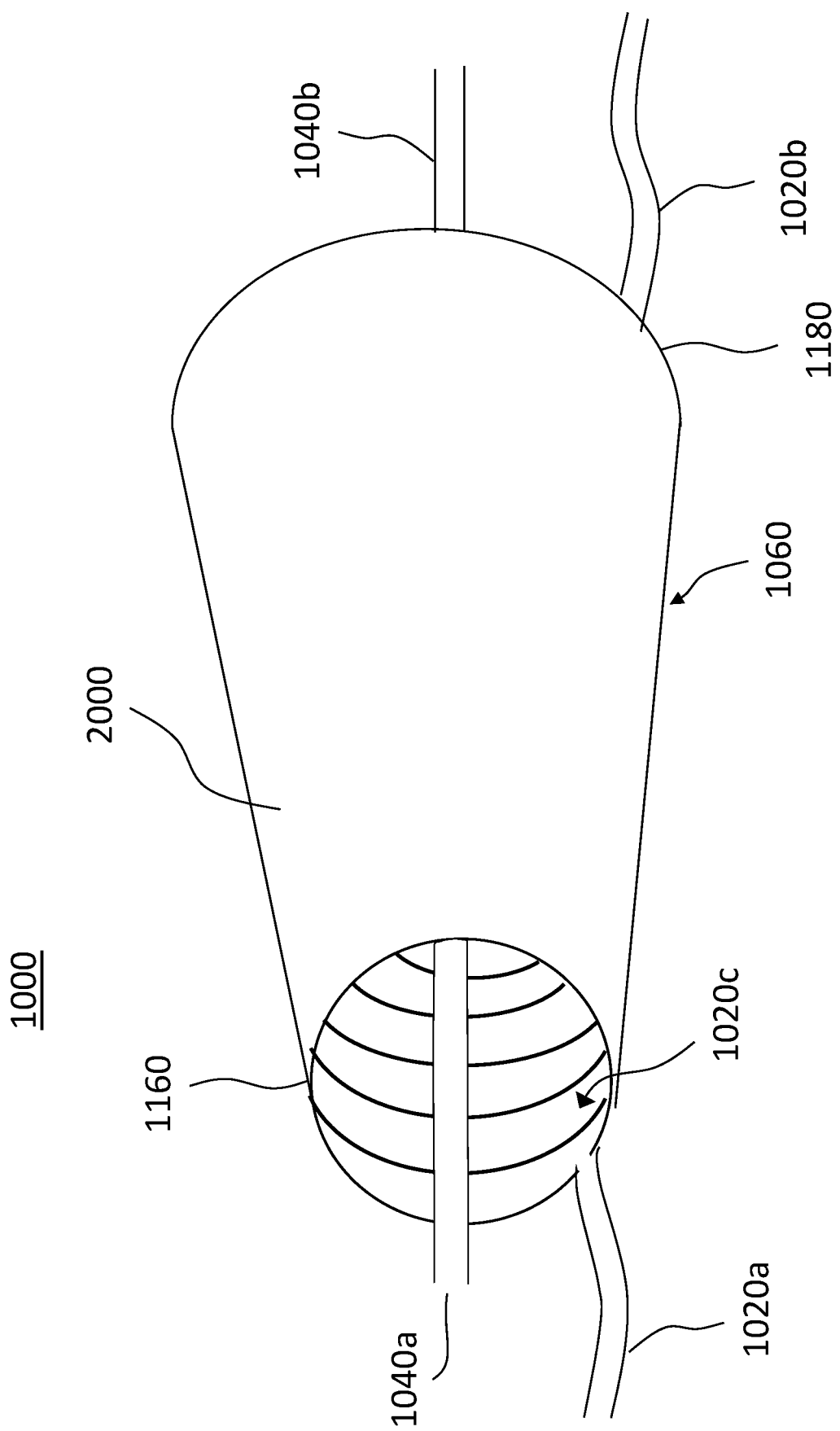
FIG. 9 is a perspective view of a tapered actuation line storage apparatus, according to some embodiments.

FIG. 9 shows a tapered actuation line storage system 1000, according to some embodiments. As shown, the actuation line storage portion 1060 can include a diametric taper. In other terms, the intermediate portion 1020c of the first actuation line 1020 can be tapered such that a first end 1160 of the intermediate portion 1020c has a smaller diameter than a second end 1180 of the intermediate portion 1020c, or vice versa. Similarly, the release material 2000 can also be tapered. In some instances, a diametric taper can allow for easier storage within the deployment system 100 or, more specifically, within the deployment handle 300. Though FIG. 9 shows the tapered slack pattern of the intermediate portion 1020c in a looped configuration, the tapered slack pattern can also define the figure eight configuration, as discussed above, or any other suitable configuration as desired.

Though looped slack patterns and figure eight slack patterns are described above, other slack patterns are also possible. For example, in some embodiments, the slack pattern can define an accordion folding of the intermediate portion 1020c of the first actuation line 1020. In other terms, the first actuation line 1020 may be folded or generally pleated in a repeating pattern. In other embodiments, the slack pattern can define more than one configuration such as, for example, both looped and figure eight configurations.

Though the actuation line storage portion 1060 has been described above with respect to the first actuation line 1020, the second actuation line 1040 may also optionally include a storage portion, as shown in FIG. 1. Similar embodiments can also be realized for any additional number of actuation lines, as desired. For example, the examples and embodiments described above can be used for an optional third actuation line, fourth actuation line, and any other amount of actuation lines as desired.

In some embodiments, a method of deploying an expandable, implantable medical device includes tensioning the first actuation line 1020 or the first portion 1020a of the first actuation line 1020 to actuate the first actuation element E1. For example, to release the constraining sleeve 400 from the medical device 300 or to expand the medical device 300. The method also includes tensioning the second actuation line 1040 or the first portion 1040a of the second actuation line 1040 to actuate the second actuation element E2. For example, to pull back or retract the constraining sleeve 400 from the medical device 300. In some embodiments, tension applied to the first portion 1040a of the second actuation line 1040 immediately translates to tension applied to both the intermediate portion 1040c and the second portion 1040b of the second actuation line 1040. Thus, the second actuation element E2 is initiated before the first actuation element E1. Tension applied to the first portion 1020a of the first actuation line 1020 translates to the intermediate portion 1020c of the first actuation line 1020 but does not immediately translate to the second portion 1020b of the first actuation line 1020. Thus, the second actuation element E2 is initiated after complete unwinding of the slack pattern of the first actuation line 1020.

The actuation line storage system 1000 described above can be formed in a variety of ways. In some instances, wire, string, fiber or another suitable actuation line is wrapped around a cylindrical mandrel such as a stainless-steel mandrel. An appropriate length of tubing, such as fluorinated ethylene propylene (FEP) tubing, is then slid over the fiber and mandrel. Heat may then be applied to the tubing to shrink the tubing down over the actuation line. This ensures the tubing remains in place over the mandrel during further processing. The mandrel is then placed in an oven for an amount of time suitable to adequately adhere the fiber to the inside surface of the tubing. Upon removal from the oven, the tubing and fiber are allowed to cool to room temperature, after which the tubing and fiber can be removed from the mandrel and placed inside of the delivery system 100.

Persons skilled in the art will readily appreciate that various aspects of the present disclosure can be realized by any number of methods and apparatus configured to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

What is claimed is:

1. A medical device deployment apparatus that employs a first actuation line and a second actuation line, whereby a delay is sought between initiation of actuation of the first actuation line and initiation of actuation of the second actuation line, the medical device deployment apparatus comprising, prior to actuation, the first actuation line including a first portion, a second portion, and an intermediate portion extending between the first portion and the second portion, the intermediate portion configured in a slack pattern comprising sequentially aligned multiple loops;
   wherein the multiple loops in the intermediate portion provide predefined slack to delay linear actuation of the first actuation line when tension is applied to both the first and second actuation lines;
   the medical device deployment apparatus further comprising a release material, wherein the multiple loops are releasably coupled to the release material to maintain the sequentially aligned multiple loops prior to actuation.

2. The medical device deployment apparatus of claim 1, wherein the release material comprises a tube.

3. The medical device deployment apparatus of claim 2, wherein the multiple loops are releasably adhered inside of the tube.

4. The medical device deployment apparatus of claim 2, wherein the second actuation line is routed through the tube.

5. The medical device deployment apparatus of claim 1, wherein the multiple loops define a repeating figure-8 pattern.

6. A medical device deployment apparatus that employs a first actuation line and a second actuation line, whereby a delay is sought between initiation of actuation of the first actuation line and initiation of actuation of the second actuation line, the medical device deployment apparatus comprising, prior to actuation, the first actuation line including a first portion, a second portion, and an intermediate portion extending between the first portion and the second portion, the intermediate portion being releasably coupled to a release material in the form of sequential multiple windings to maintain the sequential multiple windings prior to actuation;
   wherein the multiple windings in the intermediate portion provide predefined slack to delay linear actuation of the first actuation line when tension is applied to both the first and second actuation lines.

7. The medical device deployment apparatus of claim 6, wherein the release material comprises a tube.

8. The medical device deployment apparatus of claim 6, wherein the release material comprises a sheet.

9. The medical device deployment apparatus of claim 6, wherein the multiple windings comprise multiple loops.

10. The medical device deployment apparatus of claim 9, wherein the multiple windings comprise a figure-8 configuration.

11. The medical device deployment apparatus of claim 6, wherein the multiple windings comprise an accordion folding of the second actuation line.

12. A fiber storage system for an actuation assembly, the fiber storage system comprising:
   a first actuation line defining a first portion, a second portion, and an intermediate portion extending between the first portion and the second portion, the intermediate portion configured in a slack pattern; and
   a release material having an inner surface defining an inner lumen of the release material, wherein the slack pattern at the intermediate portion of the first actuation line is maintained by the intermediate portion being releasably coupled to an inner aspect of the release material such that, upon tensioning the first portion of the first actuation line, the intermediate portion is serially released from the inner aspect of the release material according to the slack pattern without transferring tension to the second portion of the first actuation line.

13. The system of claim 12, wherein the slack pattern includes a helical portion.

14. The system of claim 12, wherein the slack pattern includes multiple sequentially aligned loops.

15. The system of claim 12, wherein the slack pattern includes multiple, sequentially aligned figure-8's.

16. The system of claim 12, wherein the slack pattern includes a diametric taper.

17. The system of claim 12, further comprising a second actuation line defining a first portion, a second portion, and an intermediate portion extending between the first portion and the second portion of the second actuation line, the second actuation line extending through the slack pattern of the first actuation line.

18. The system of claim 17, wherein the first portion of the first actuation line is operably coupled to the first portion of the second line such that tension is applied concurrently to the first actuation line and the second actuation line, and
   wherein, in response to applying the tension concurrently to the first actuation line and the second actuation line, the slack pattern in the intermediate portion of the first actuation line facilitates tensioning of the first portion of the first actuation line without tensioning the second portion of the second actuation line.

19. The system of claim 12, wherein the release material includes a hollow tube having an inner lumen defining the inner aspect of the release material.

20. A medical device system comprising:
   a fiber storage including:
      a first actuation line defining a first portion, a second portion, and an intermediate portion extending between the first portion and the second portion, the intermediate portion configured in a slack pattern,
      a second actuation line defining a first portion, a second portion, and an intermediate portion, the second actuation line extending through the slack pattern of the first actuation line, and
      a release material having an inner surface defining an inner lumen of the release material, the intermediate portion of the first actuation line being releasably maintained in the slack pattern by an inner aspect of the release material such that, upon tensioning the first portion of the first actuation line, the intermediate portion is serially released from the inner aspect of the release material according to the slack pattern without transferring tension to the second portion of the first actuation line;
   an expandable medical device; and
   a sleeve diametrically constraining the medical device;
   wherein the first actuation line is configured to release the sleeve and the second actuation line is configured to retract the sleeve.

21. A method of deploying an expandable medical device of a medical device system, the method comprising:

tensioning a first actuation line of the medical device system to pull back a sleeve diametrically constraining the expandable medical device from the expandable medical device, wherein the first actuation line has a first portion, a second portion, and an intermediate portion extending between the first portion and the second portion of the first actuation line, and wherein the intermediate portion is releasably coupled to an inner aspect of a release material to maintain the intermediate portion in a slack pattern; and tensioning a second actuation line of the medical device system to release the sleeve from the expandable medical device, wherein the second actuation line extends through the slack pattern of the intermediate portion of the first actuation line;

wherein the second actuation line has a first portion, a second portion, and an intermediate portion extending between the first portion and the second portion of the second actuation line, wherein tension applied to the first portion of the second actuation line translates to tension applied to both the intermediate portion of the second actuation line and the second portion of the second actuation line, and wherein tension applied to the first portion of the first actuation line is initially translated to the intermediate portion of the first actuation line according to the slack pattern without being immediately translated to the second portion of the first actuation line.

22. A medical device deployment apparatus that employs a first actuation line and a second actuation line, whereby a delay is sought between initiation of actuation of the first actuation line and initiation of actuation of the second actuation line, the medical device deployment apparatus comprising, prior to actuation, the first actuation line being releasably coupled to a release material in the form of sequential multiple windings;

wherein the multiple windings comprise an accordion folding of the second actuation line and provide pre-defined slack to delay linear actuation of the first actuation line when tension is applied to both the first and second actuation lines.

23. A fiber storage system for an actuation assembly, the fiber storage system comprising:

a first actuation line defining a first portion, a second portion, and an intermediate portion extending between the first portion and the second portion, the intermediate portion configured in a slack pattern that includes a diametric taper; and a release material having an inner surface defining an inner lumen of the release material, the intermediate portion of the first actuation line being releasably maintained in the slack pattern by an inner aspect of the release material such that, upon tensioning the first portion of the first actuation line, the intermediate portion is serially released from the inner aspect of the release material according to the slack pattern without transferring tension to the second portion of the first actuation line.

* * * * *